US007372262B2

(12) United States Patent
Bertozzi et al.

(10) Patent No.: US 7,372,262 B2
(45) Date of Patent: May 13, 2008

(54) METHODS AND SYSTEMS FOR ACTIVE NON-INTRUSIVE INSPECTION AND VERIFICATION OF CARGO AND GOODS

(75) Inventors: William Bertozzi, Lexington, MA (US); Gustavo Bottan, Lexington, MA (US); Robert J. Ledoux, Harvard, MA (US)

(73) Assignee: Passport Systems, Inc., Acton, MA (US)

( * ) Notice: Subject to any disclaimer, the term of this patent is extended or adjusted under 35 U.S.C. 154(b) by 0 days.

(21) Appl. No.: 11/557,245

(22) Filed: Nov. 7, 2006

(65) Prior Publication Data

US 2007/0145973 A1    Jun. 28, 2007

Related U.S. Application Data

(60) Provisional application No. 60/734,915, filed on Nov. 9, 2005.

(51) Int. Cl.
*G01V 3/00* (2006.01)
(52) U.S. Cl. .................................. 324/300; 324/307
(58) Field of Classification Search ........ 324/300–322; 378/57, 58
See application file for complete search history.

(56) References Cited

U.S. PATENT DOCUMENTS

| | | | |
|---|---|---|---|
| 3,496,357 A | 2/1970 | Weinzierl | |
| 4,415,804 A | 11/1983 | Sowerby | |
| 4,446,568 A | 5/1984 | Williams et al. | |
| 4,788,704 A | 11/1988 | Donges et al. | |
| 4,941,162 A | 7/1990 | Vartsky et al. | |
| 5,115,459 A | 5/1992 | Bertozzi | |
| 5,247,177 A | 9/1993 | Goldberg et al. | |
| 5,323,004 A * | 6/1994 | Ettinger et al. | 250/336.1 |
| 5,420,905 A | 5/1995 | Bertozzi | |
| 5,600,303 A | 2/1997 | Husseiny et al. | |
| 5,600,700 A | 2/1997 | Krug et al. | |

(Continued)

FOREIGN PATENT DOCUMENTS

WO      WO-99/39189      8/1999

OTHER PUBLICATIONS

Bertozzi, William, Poster: Material Identification and Object Imaging using Nuclear Resonance Fluorescence, Jul. 18, 2003, MIT, Dept. of Energy's Ofc of Nuclear Physics Workshop on the Role of the Nuclear Physics Research Community in Combating Terrorism.

(Continued)

*Primary Examiner*—Brij Shrivastav
(74) *Attorney, Agent, or Firm*—Foley Hoag LLP

(57) ABSTRACT

Systems and methods are disclosed herein for the non-intrusive inspection and/or verification of cargo. In an exemplary embodiment, an elemental signature is determined at a first point in a supply chain and transmitted to a second point in the supply chain. When the goods arrive at the second point, the elemental signature of the goods may be measured and verified against the original elemental signature. In another embodiment, an elemental signature may be measured to verify the origin or identity of the goods. In some embodiments such elemental signatures are inherent to the shipped goods and/or their packaging. In other embodiments, elemental signatures are applied to the shipment as tag materials.

13 Claims, 1 Drawing Sheet

U.S. PATENT DOCUMENTS

| | | |
|---|---|---|
| 5,642,393 A | 6/1997 | Krug et al. |
| 5,974,150 A * | 10/1999 | Kaish et al. ............... 713/179 |
| 6,018,562 A | 1/2000 | Willson |
| 6,088,423 A | 7/2000 | Krug et al. |
| 6,108,396 A | 8/2000 | Bechwati et al. |
| 6,175,609 B1 | 1/2001 | Edic et al. |
| 6,345,113 B1 | 2/2002 | Crawford et al. |
| 6,370,222 B1 * | 4/2002 | Cornick, Jr. ............... 378/57 |
| 6,442,233 B1 | 8/2002 | Grodzins et al. |
| 7,120,226 B2 * | 10/2006 | Ledoux et al. ............... 378/57 |
| 2004/0001568 A1 | 1/2004 | Impson et al. |
| 2004/0109532 A1 | 6/2004 | Ford et al. |
| 2005/0094765 A1 | 5/2005 | Bijjani et al. |
| 2005/0111619 A1 | 5/2005 | Bijjani et al. |

OTHER PUBLICATIONS

Degener et al., Dipole Excitations in 48Ti Studied by Nuclear Resonance Fluorescence, Nuclear Physics A513 (1990) 29-42.

Metzger, Electric Dipole Transitions from the 2.6 MeV Septuplet in Bi209, Physical Review 187 (1969) 1680-1682.

* cited by examiner

METHODS AND SYSTEMS FOR ACTIVE NON-INTRUSIVE INSPECTION AND VERIFICATION OF CARGO AND GOODS

REFERENCE TO RELATED APPLICATIONS

This application claims the right of priority to U.S. Provisional Application No. 60/734,915, filed Nov. 9, 2005, which is hereby incorporated herein by reference.

BACKGROUND OF THE INVENTION

1. Field of the Invention

This invention relates to systems and methods for the use of active non-intrusive inspection technology for the verification of cargo and/or goods.

2. Background Information

Manufactured goods, raw materials, equipment, provisions, supplies, and a variety of other items are routinely shipped throughout the world by land, air, sea, and even space. Often such items are shipped in sealed containers, such as cargo containers. The need for effective means of identifying and/or verifying the contents of such containers is of importance to any concern, whether government or private commerce, that transports or handles them. For example:

Customs and law enforcement may wish to detect and interdict contraband, drugs, and terror threats such as explosives or nuclear material.

Recipients of merchandise may wish to verify that the correct goods are being delivered.

Shippers may wish to ensure goods are transported and stored safely and correctly.

Producers and buyers may wish to make certain that received goods are what they are supposed to be and not counterfeit.

Other instances in which identification and verification of goods may be paramount will be readily recognized by those skilled in the art. Yet such identification and verification may present difficulties that are cost-prohibitive or impractical due to various factors, such as:

Verification of contents by manual inspection may be cost-prohibitive and introduce impracticable delays in the shipment of goods.

Verification by destructive techniques that require unpacking or destruction of the container may not be practicable.

Containers may be tamper-proof or otherwise difficult or cumbersome to open.

The goods for which verification is desired may be buried deep within a container or are otherwise difficult to reach.

The environment may be dangerous or otherwise unsuitable for human inspection.

In the above scenarios, as well as others that will be recognized by those skilled in the art, non-destructive and non-intrusive means of identification and/or verification of the contents of a container may be desirable.

In any flow of goods, there is generally a supply chain that may include an origin (e.g., a producer, manufacturer, shipper, or the like); a transit route (which may include packing, shipping, forwarding, temporary storage, receiving, etc.); and an end point marked by the acceptance of delivery by a recipient, such as a customs inspection site, a purchaser, or an end-user. Non-intrusive means for identification of goods may be useful at multiple points along this supply chain. Currently, for reasons such as those listed above, there may be no practicable way to ascertain the origin, quality, and other characteristics of goods at multiple points in a supply chain. Further, in many cases visual inspections or other current methods of analysis may not be able to distinguish between genuine and counterfeit goods.

SUMMARY OF THE INVENTION

We have developed systems and methods for non-intrusive identification and/or verification of shipped goods that do not require opening the container, package, enclosure, wrapping, or other enclosing material. The systems and methods described herein may increase the security of a supply chain without adding impracticably to the cost or time of transactions involving the shipment of goods.

An advantage of the systems and methods we have developed is that they may allow parties in a supply chain to ensure that they are shipping and/or receiving genuine and correct goods. Further, the systems and methods disclosed may make it possible to do so without opening containers or enclosures, which could impracticably delay the flow of goods and increase transaction cost and time. The systems and methods described herein also may allow parties in the supply chain to be certain that there has been no tampering with or any change to the contents and condition of the goods in the container. The systems and methods described herein employ an elemental signature that can identify or provide details of the contents in the container. As discussed further below, this elemental signature may be inherent to the container and/or its contents, or it may be applied or added to the container or its contents during manufacture, upon packing, or at a later point in the supply chain.

In some situations, it may be desirable to have enough information for a party in the supply chain to certify that the shipment is genuine and not modified in any way, without disclosing the contents of the container to that party. For example, such verification without disclosure of the contents might be advantageous in military, diplomatic, or other confidential or sensitive situations. For these cases, as discussed further below, an elemental signature may be used that validates the provenance of the container and/or its contents without necessarily being descriptive of the contents or allowing identification of the contents. Such an elemental signature may be used to identify the container and its contents as a whole, without specific descriptors. A system employing such elemental signatures may provide a rapid and efficient way to be certain that the shipment has arrived as intended, and has not been changed or tampered with.

In an exemplary embodiment, an elemental signature of a cargo container or its contents may be measured at a first point in a supply chain. The elemental signature may be digitally encoded and transmitted to a later point in the supply chain. When the container arrives at the later point, the elemental signature may be measured again and compared to the elemental signature measured at the first point. Thus the invention may provide a way to verify that the container's contents have not been tampered with or otherwise altered in transit.

In another exemplary embodiment, an expected elemental signature may be predicted based upon the elemental or isotopic composition of the container and its contents, and/or upon the spatial distribution of those contents within the container. For example, the predicted elemental signature may be computed based upon a shipping manifest or other listing of the container's contents. At any point in a supply chain, the elemental signature of the container and its contents may be measured and compared against the expected elemental signature. In this way, the contents of the container may be verified non-intrusively.

In another exemplary embodiment, a "tag material" may be introduced to the shipping container and/or its contents at the point of manufacture, packing, or other point in the supply chain. Such tag material may be selected to uniquely identify the point of origin or the manufacturer or supplier of the goods. At any later point in the supply chain, an elemental signature of the tag material may be measured, thus verifying the origin or manufacturer or supplier identified by the tag material.

In still another exemplary embodiment, multiple tag materials may be disposed in the container such that a certain condition triggers a measurable change in elemental signature that may be used to detect whether the condition has occurred.

BRIEF DESCRIPTION OF THE DRAWINGS

The description below refers to the accompanying drawings, of which.

DETAILED DESCRIPTION OF ILLUSTRATIVE EMBODIMENTS

Figure 1:
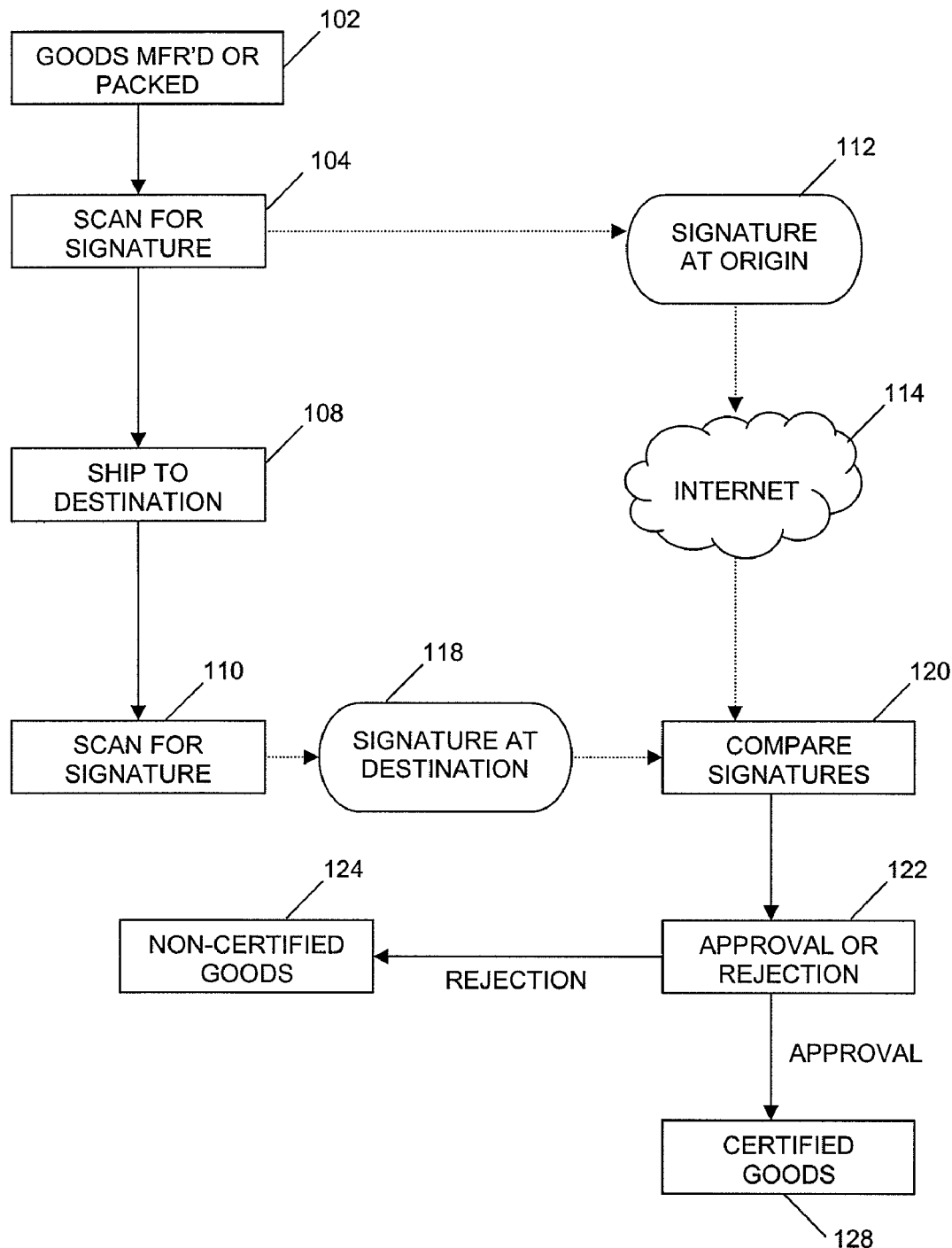
FIG. 1 illustrates an exemplary procedure for the verification of goods using embodiments of the systems and methods described herein.

To provide an overall understanding, certain illustrative embodiments will now be described; however, it will be understood by one of ordinary skill in the art that the devices and methods described herein can be adapted and modified to provide devices and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, specified, interchanged, and/or rearranged without departing from the disclosed devices or methods. Additionally, the shapes and sizes of components are also exemplary, and unless otherwise specified, can be altered without affecting the disclosed devices or methods.

The systems and methods described herein may employ Nuclear Resonance Fluorescence Imaging (NRFI), measurements of effective atomic number (effective Z), X-ray transmission imaging, measurements made by other active non-intrusive interrogation technologies, or combinations of such measurements as the basis for non-intrusive identification and/or verification of container contents.

NRFI measurements may exploit the fact that a beam of photons incident on a target can excite in the target nuclear resonances or states that subsequently fluoresce. The excitation spectrum and the resulting emission spectra are uniquely determined by the particular isotopes contained in the target. When detected by systems of detectors or detector arrays capable of resolving spatial information, these spectra allow for a measurement of the spatial distribution of isotopes contained in the irradiated volume. Some exemplary systems for employing NRFI measurements in non-intrusive scanning applications are discussed in U.S. Pat. No. 5,115,459, Explosives Detection Using Resonance Fluorescence of Bremsstrahlung Radiation, U.S. Pat. No. 5,420,905, Detection of Explosives and Other Materials Using Resonance Fluorescence, Resonance Absorption, and Other Electromagnetic Processes with Bremsstrahlung Radiation, and U.S. Pat. No. 7,120,226, Adaptive Scanning Of Materials Using Nuclear Resonance Fluorescence Imaging, the contents of which are incorporated herein by reference.

Apart from NRFI measurements (which may exploit characteristic frequencies of resonant scattering to identify isotopes present in a sample under scan), analysis of the energy spectrum of photons scattered non-resonantly from a target under scan can also yield information about the target's composition. For example, as described in U.S. patent application Ser. No. 11/177,758, issued as U.S. Pat No. 7,286,638, incorporated herein by reference, analysis of non-resonant scattering of photons can yield a measurement of the average or effective atomic number (effective Z) of the illuminated portion of a target. Such non-resonant spectra, when detected by systems of detectors or detector arrays capable of resolving spatial information, can yield a measurement of the spatial distribution of the effective Z in a target.

An advantage of using NRFI and/or effective-Z non-intrusive scanning methods is that verification may be achieved quickly enough to make sure that transit of goods is not significantly delayed.

Because the signal obtained from either a NRFI or an effective-Z scan depends upon the composition of the material being scanned, NRFI or effective-Z scans can be used to generate an "elemental signature" of a target under scan. (Although in the exemplary embodiments a cargo container is used for illustration of the principles, it should be appreciated that any shipment of any kind may be verified using these principles, including air, sea, or land cargo, luggage, goods shipped by air freight, etc.)

It should be noted that a signal obtained by NRFI may contain isotopic as well as elemental information. Thus the so-called "elemental signature" may indeed be an isotopic signature where NRFI measurement is used. Further, in some embodiments of the invention the signature may be a density measurement or projected density map obtained by traditional X-ray transmission imagery. Thus embodiments of the invention described herein may use effective-Z signatures, NRFI signatures, or even X-ray transmission signatures, or a combination of such signatures, to non-intrusively verify the contents or origin of any shipment. The term "elemental signature" will be used generically herein to refer to all such signatures, whether obtained from effective-Z, NRFI, or X-ray transmission measurements, or from a combination of such measurements. The term "elemental signature" should also be understood to include any signature obtained by analyzing photons scattered from or transmitted through a target to determine the elemental or isotopic composition of some or all of the target. Such an elemental signature may include a bulk measurement of density, elemental or isotopic composition; a total or relative abundance of one or more elemental or isotopic components; and/or a 1-D, 2-D, or 3-D spatial distribution of density, elemental, or isotopic composition or total or relative abundance of components throughout the target or a portion of the target. Particular embodiments of such elemental signatures are discussed further below.

Any elemental signature may correspond to a single item in the cargo container, to the cargo container as a whole, or to a 3-D sub-volume (voxel) of the container and its contents, or any other relationship between them. In some embodiments, an elemental signature may include a list of isotopes with their total or relative abundances, as measured by NRFI techniques. In some embodiments an elemental signature may include a list of NRF spectral lines, i.e. energies and absolute or relative signal intensities that again may correspond to the entire container, a container voxel, or any portion of the container's contents. In further embodiments, a single isotopic abundance or even a single spectral line may be all that is required for the elemental signature. Similarly, elemental signatures may include effective-Z information corresponding to the entire cargo container, a container voxel, or any portion of the container's contents. Because both NRFI and effective-Z measurements allow for three-dimensional mapping, the elemental signature of a cargo container (or of any portion or subunit thereof) may be a three-dimensional isotopic map, obtained at any resolution necessary for a particular application. It will be appreciated that for some applications, a rough NRFI or effective-Z measurement of the cargo container as a whole may be all that is desired, while for other applications a more detailed spatial elemental signature may be useful.

FIG. 1 provides an illustration of a supply chain in which exemplary embodiments of the systems and methods described may be employed. Step 102 represents the origin of the supply chain, at which the items to be shipped (such as raw materials, manufactured goods, or any other materials) are manufactured and/or packed into a cargo container.

At step 104, a NRFI scanning system or an effective-Z scanning system is employed to determine the elemental signature of the cargo container and/or its contents at the origin. The elemental signature at the origin, represented in FIG. 1 by item 112, may be determined in any of several ways.

In one exemplary method, elemental signatures of individual items, individual containers, or other subunits of the container's contents are known. For example, these may be measured using an NRFI or effective-Z measurement system at the site of manufacture or at the packing site. Or, they may be determined based upon the known composition of the goods or materials to be shipped. For example, for manufactured items an a priori elemental signature may be provided, with a certain tolerance, as a manufacturing specification of the item, so that an individual elemental signature need not be measured for every unit.

When the elemental signatures of the subunits of the container's contents are known, together with a known packing location of each individual subunit within the container, an a priori spatial elemental signature of the entire container can be obtained. For example, the NRFI elemental signature of a manufactured item may be measured and recorded prior to packing the item in the shipping container. Knowledge of the distribution of this manufactured item in a container would yield a predicted three-dimensional map of an NRFI scan of the container; i.e. a predicted spatial distribution of NRFI signals obtained from the container.

In some embodiments, the predicted elemental signature itself may be adopted as the elemental signature 112 at the origin of the goods. In alternative embodiments, the elemental signature may be measured separately at the origin and compared to the predicted elemental signature, in order to provide an extra check that the goods were correctly manufactured and/or packed.

Alternatively, the elemental signatures of the individual items in the shipping container may be unknown or not considered. Instead, an average signal over the entire container or the spatial distribution of the measured signals from the container may be measured at the origin and used to generate the elemental signature 112 for a particular container at the origin.

An original elemental signature 112 measured at the origin of goods (or at any point in the supply chain), or a predicted or computed a priori elemental signature as described above, can be digitally encoded and transmitted, or otherwise transmitted, to any later point in the supply chain. For example, as illustrated in FIG. 1, the elemental signature 112 may be transmitted via the internet 114 to a destination of the shipment, which can be any intermediate or final destination. Other means of transmission known to one of ordinary skill in the art may be used. In addition, the system and method may be adapted to use before and after goods are stored as well as or rather than transported, and references to origin or destination herein may be understood to encompass or refer to the times before and after the goods undergo storage as well.

Meanwhile, as represented in FIG. 1 by step 108, the cargo container is shipped. At the destination, as represented by step 110, or at an intermediate point, a second NRFI or effective-Z scanning system is employed to determine the elemental signature 118 at the destination or intermediate point. At step 120, the elemental signature 112 determined at the origin is compared with the elemental signature 118 determined at the destination or intermediate point. The comparison may be performed automatically by a processor located at the destination or intermediate point or at any remote location (i.e. connected to a processor at the destination or intermediate point via the internet). The processor may be programmed with heuristics for determining whether the elemental signature 118 at the destination or intermediate point matches the elemental signature 112 at the original to within some specified tolerance. In an exemplary embodiment, the tolerance for a match is based upon the signal-to-noise ratio of the scan taken at the origin. The tolerance for a match may thus be based upon statistical analysis of the elemental signature 112 determined at the origin and the elemental signature 118 determined at the destination or intermediate point. For example, the processor may be programmed to identify a failure to match if one or more features of the elemental signature 118 determined at the destination or intermediate point deviates by more than one sigma from the corresponding one or more features of the elemental signature 112 determined at the origin. Features that may be considered in this determination may include the number of counts in particular spectral lines, total or relative abundances of particular isotopes or elements, estimated effective-Z in the entire container or a portion thereof, and/or any information that may be extracted from the raw scattering or transmission data obtained in a scan, together with the corresponding statistical error bars.

In some embodiments, there may be no measurement of an elemental signature 112 at the origin. Instead, as described above, an a priori signature may be computed and transmitted to the destination or intermediate point for comparison with the elemental signature 118 determined at the destination or intermediate point. Or, in an alternative embodiment, a predicted elemental signature may be computed at the destination or intermediate point based upon a shipping manifest, certificate, or other information provided with the shipment or ahead of time. In such an embodiment the elemental signature 118 determined at the destination or intermediate point can be compared with the predicted elemental signature in order to verify that the container's contents are what they are supposed to be.

In the event that the elemental signature measured 118 determined at the destination or intermediate point meets the criteria of approval (whether by comparison with a predicted elemental signature computed anywhere in the supply chain or an elemental signature measured at the origin of the shipment), as represented by step 128, the shipment may be certified for delivery or such further processing as is appropriate. In the event the elemental signatures do not match, represented by step 124, the shipment may be flagged for return to the sender, re-scanning, manual inspection, or other action appropriate to the application. A mismatch between the elemental signature measured at two points in the supply chain (or between a predicted elemental signature and a measured elemental signature) can indicate that the container has been tampered with or the goods modified. In contrast, a match between the elemental signature measured at two points in the supply chain (or between a predicted elemental signature and a measured elemental signature) can be considered verification of the integrity of the shipment.

In one embodiment, at the end point of a supply chain, there may be a certified receipt listing the expected contents of the shipment. A NRFI scan can determine the isotopic content and/or spatial distribution of isotopes within the shipment and compare them against the NRFI signals that would be expected given the cargo listed in the receipt. In this way it is possible to determine the contents of the container and match them against a shipping list or manifest, if desired.

An example of the use of an elemental signature to verify a shipment of goods is a scenario in which it is desired to verify a shipment of consumer electronics. The elemental signature may include an isotopic composition of the particular electronics to be shipped and associated packaging, either determined prior to packing by NRFI analysis, or computed a priori from knowledge of the composition of the electronics and packaging. If the container is known to be loaded only with those electronics and packaging, the entire container must have a signature which is consistent with those contents. Thus it may be confirmed at the point of origin that the contents were loaded with the proper products. Further, NRFI scans later in the supply chain could re-confirm that no modifications have taken place.

In another example, the shipment to be confirmed may contain a heterogeneous mixture of materials for which no a priori distribution is known or predicted. In such a scenario, an effective-Z scan may be made at the origin of the supply chain to determine an elemental signature of the container. At a later point in the supply chain, another effective-Z scan may be performed to verify the elemental signature and determine whether the contents have been modified during transit.

Elemental signatures can be used in a wide range of applications for the non-intrusive inspection and/or verification of goods. As mentioned above, they can be obtained for a cargo container and its goods as a whole, or for any subunit within the container. In such embodiments, the elemental signature corresponds the isotopic content of the cargo and container materials themselves. It is also possible, however, to read and detect elemental signatures of other items attached to the products, cargo, or to the container. These can be introduced by the manufacturer, shipper, or other parties in the supply chain, to ensure their work was completed and certify its quality, quantity or validity. Their specific elemental signatures can also be used to produce certificates of authenticity or of non-tampering. Alternative embodiments exploit the addition of such "tag materials" to a shipping container's contents (including goods and/or packing material). Such tag materials could provide an engineered elemental signature that can be specific to product, manufacturer, origin, manufacture date or shipping date, or any other characteristic of the containers contents that it may be desirable to verify with a non-intrusive scan.

Cargo packed with such a tag material can be verified by performing a NRFI or effective-Z scan that identifies the presence of the tag material in the shipment. Tag materials may be mixtures of known isotopes in known proportions. A tag material may be a common material, but preferably it is specially selected such that the tag material's elemental signature is not otherwise common in the particular cargo shipped in a particular application, or in cargo, cargo containers, or packing materials generally. An example of such a tag is $^{11}$Boron, which is not widely found in commercial products and has multiple strong NRF states.

Further, manufacturers and suppliers may find it advantageous to develop identifying elemental signatures for their products. Such tag materials may be added in bulk to shipments, included in packing materials, incorporated directly into manufactured goods, or incorporated into solutions or emulsions to be applied to the exterior of items or containers, e.g. by spray-painting.

Tag materials as described above may be used to verify the provenance of shipped goods or the origin or a transit point of the shipment. For example, the composition (or the NRFI or effective-Z elemental signature) of a tag material associated with a particular source of goods may be known at a destination or intermediate point in a supply chain. At that destination or intermediate point, the shipment may be scanned with a NRFI or effective-Z scanning system, and the presence of the tag material detected. Thus, the origin of the goods may be verified at any point in the supply chain where the material or its elemental signature is known; it is not necessary for the identity of the goods, or even their isotopic composition, to be known at the stage in the supply chain at which the verification is occurring. This may be desirable, for example, in military applications, in which it may be useful to verify the shipment along the supply chain without revealing its contents to parties in the supply chain. It may also be desirable in diplomatic or intelligence operations to verify shipments of electronics or any other covert or secret equipment without revealing their contents to parties in the supply chain.

In alternative embodiments, the systems and methods described herein may be used to determine whether a particular condition has occurred between two points in a supply chain. In such an embodiment, one or more tag materials may be disposed in the shipment such that when a particular event or condition arises during storage or transit at any point in the supply chain, the elemental signature of the tag material is altered. By detecting this change (or the absence of such a change) at a later point in the supply chain, it can be determined whether the event or condition occurred. Suitable changes in the elemental signature of the tag material include any change that may be detected by measurement of the elemental signature, including an alteration in the spatial distribution of elemental and/or isotopic composition and/or spatial distribution of density.

In an example of such an embodiment, the tag material is disposed in a condition-sensing device in which two tag materials having distinct elemental signatures are separated by a valve, membrane, or other barrier that will breach in the event a certain condition occurs. For example, the barrier may be a valve coupled to an external sensor such that the valve opens at a certain threshold temperature (either upper limit, lower limit, or both), humidity (either upper limit, lower limit, or both), vibration or acceleration threshold, etc. Sensors for any other measurable condition, such as the presence of a particular gas (such as carbon dioxide), exposure to a certain chemical or biological condition, or exposure to radiation, may be employed to trigger the opening or breaching of the barrier.

In an exemplary embodiment the tag materials may be gas or liquid such that they mix automatically upon breaching of the barrier. In other embodiments, the condition-sensing device may also include stirring or mixing means (such as a stirring paddle or blade) that mixes solid tag materials upon triggering of the selected sensor condition. In some embodiments in which solid tag materials are used, such as powdered tag materials, a barrier between the tag materials may not be required; in such embodiments the materials would mix only upon the triggering of the stirring or mixing means.

The mixing of the multiple tag materials creates a new distribution of elements, isotopes, or density in the volume of the condition-sensing device upon triggering of the device by occurrence of the condition. Where the elemental signature is measured at any point in the supply chain with sufficient spatial resolution to detect such changes, they can be used to detect whether the triggering condition has occurred at any previous point in the supply chain.

Although the methods and systems have been described relative to specific embodiments thereof, they are not so limited. Obviously many modifications and variations may become apparent in light of the above teachings.

While the systems and methods disclosed herein have been particularly shown and described with references to exemplary embodiments thereof, it will be understood by those skilled in the art that various changes in form and details may be made therein without departing from the spirit and scope of the disclosure. Those skilled in the art will recognize or be able to ascertain using no more than routine experimentation, many equivalents to the exemplary embodiments described specifically herein. Such equivalents are intended to be encompassed in the scope of the present disclosure.

What is claimed is:

1. A method for verifying contents of a container, comprising:
   a) obtaining a first elemental signature of said contents;
   b) obtaining a second elemental signature of said contents, comprising information about an isotopic or elemental composition of said contents determined after the container has been transported and/or stored at least in part by measurements of effective atomic number made by comparing scattering from said contents in a first energy region with scattering from said contents in at least one additional energy region;
   c) comparing the first elemental signature and the second elemental signature; and
   d) verifying the said contents upon the comparison of the first elemental signature and the second elemental signature passing a predetermined test.

2. The method of claim 1, wherein the contents comprise a tag material, and the first and second elemental signatures comprise elemental signatures of the tag material.

3. The method of claim 1, wherein the second elemental signature further comprises information about an spatial distribution of the contents of the container.

4. The method of claim 1, wherein the first elemental signature comprises information calculated or predicted based at least in part upon the isotopic or elemental composition of the contents without measurements of effective atomic number of the contents.

5. The method of claim 1, wherein the first elemental signature comprises information determined at least in part by measurements of effective atomic number of the contents.

6. A method for analyzing contents of a container, comprising:
   a) obtaining a first elemental signature of said contents;
   b) obtaining a second elemental signature of said contents, comprising information about an isotopic or elemental composition of said contents determined after the container has been transported and/or stored at least in part by at least one of Nuclear Resonance Fluorescence imaging, measurements of effective atomic number, and X-ray transmission; and
   c) comparing the first elemental signature and the second elemental signature;
   wherein the occurrence of a predetermined environmental condition is detected by a sensor during transport and/or storage, and based upon the detection of the said predetermined environmental condition during transport and/or storage, the spatial distribution of the contents in the container is altered, and
   wherein the comparison of the first elemental signature and the second elemental signature detects whether the said contents have experienced the said predetermined environmental condition during transport and/or storage.

7. The method of claim 6, wherein the predetermined environmental condition is the temperature or humidity falling below a predetermined value.

8. The method of claim 6, wherein the predetermined environmental condition is the temperature or humidity exceeding a predetermined value.

9. The method of claim 6, wherein the predetermined environmental condition is vibration or acceleration falling below a predetermined value.

10. The method of claim 6, wherein the predetermined environmental condition is vibration or acceleration exceeding a predetermined value.

11. The method of claim 6, wherein the predetermined environmental condition is the presence of a particular substance exceeding a predetermined value.

12. The method of claim 1, wherein the said contents comprise a portion of the contents of the container.

13. A method for verifying contents of a container, comprising:
   a) calculating or predicting a first elemental signature of said contents, based at least in part upon an isotopic or elemental composition of the said contents, without Nuclear Resonance Fluorescence imaging measurements of the contents or measurements of effective atomic number of the contents;
   b) obtaining a second elemental signature of said contents, comprising information about the isotopic or elemental composition of said contents determined after the container has been transported and/or stored at least in part by at least one of Nuclear Resonance Fluorescence imaging, and measurements of effective atomic number made by comparing scattering from said contents in a first energy region with scattering from said contents in at least one additional energy region;
   c) comparing the first elemental signature and the second elemental signature; and
   d) verifying the said contents upon the comparison of the first elemental signature and the second elemental signature passing a predetermined test.

* * * * *